US00PP34031P3

(12) United States Plant Patent
ter Laak

(10) Patent No.: US PP34,031 P3
(45) Date of Patent: Mar. 15, 2022

(54) ***BEGONIA* PLANT NAMED 'BETESNOGAT'**

(50) Latin Name: ***Begonia boliviensis* X *Begonia tuberhyrida***
Varietal Denomination: BeTesnogat

(71) Applicant: H. M. TESSELAAR FREESIA B.V., Heerhugowaard (NL)

(72) Inventor: Wendela Antoinette ter Laak, Zandvoort (NL)

(73) Assignee: H.M. TESSELAAR FREESIA B.V., Heerhugowaard (NL)

( * ) Notice: Subject to any disclaimer, the term of this patent is extended or adjusted under 35 U.S.C. 154(b) by 0 days.

(21) Appl. No.: 17/334,415

(22) Filed: May 28, 2021

(65) Prior Publication Data

US 2021/0386005 P1 Dec. 9, 2021

Related U.S. Application Data

(60) Provisional application No. 63/126,390, filed on Dec. 16, 2020.

(51) Int. Cl.
*A01H 5/02* (2018.01)
*A01H 6/18* (2018.01)

(52) U.S. Cl.
USPC ..... Plt./347

(58) Field of Classification Search
USPC ..... Plt./344, 347
See application file for complete search history.

*Primary Examiner* — Susan McCormick Ewoldt
(74) *Attorney, Agent, or Firm* — C. Anne Whealy

(57) ABSTRACT

A new and distinct cultivar of *Begonia* plant named 'BeTesnogat', characterized by its uniform, upright to broadly outwardly spreading plant habit; freely branching habit; dark green-colored leaves; freely flowering habit; and single-type female and double-type male flowers that are reddish orange in color.

1 Drawing Sheet

Botanical designation: *Begonia boliviensis* X *Begonia tuberhyrida.*
Cultivar denomination: 'BeTesnogat'.

BACKGROUND OF THE INVENTION

The present invention relates to a new and distinct cultivar of *Begonia* plant, botanically known as *Begonia boliviensis* X *Begonia tuberhybrida*, commonly referred to as a Hybrid Tuberous *Begonia* and hereinafter referred to by the name 'BeTesnogat'.

The new *Begonia* plant is a product of a planned breeding program conducted by the Inventor in Heerhugowaard, The Netherlands. The objective of the breeding program is to create new vigorous and strong *Begonia* plants with numerous attractive flowers and good garden performance.

The new *Begonia* plant originated from a cross-pollination on Dec. 16, 2013 of a proprietary selection of *Begonia boliviensis* X *Begonia tuberhybrida* identified as code number 12-095-10, not patented, as the female, or seed, parent with a proprietary selection of *Begonia boliviensis* X *Begonia tuberhybrida* identified as code number 12-086-01, not patented, as the male, or pollen, parent. The new *Begonia* plant was discovered and selected as a single flowering plant from within the progeny of the stated cross-pollination in a controlled greenhouse environment in Heerhugowaard, The Netherlands on Jul. 2, 2014.

Asexual reproduction of the new *Begonia* plant by vegetative terminal cuttings in a controlled greenhouse environment in Heerhugowaard, The Netherlands, since Dec. 14, 2014 has shown that the unique features of this new *Begonia* plant are stable and reproduced true to type in successive generations of asexual reproduction.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BeTesnogat'. These characteristics in combination distinguish 'BeTesnogat' as a new and distinct *Begonia* plant:

1. Uniform, upright to broadly outwardly spreading plant habit.
2. Freely branching habit.
3. Dark green-colored leaves.
4. Freely flowering habit.
5. Single-type female and double-type male flowers that are reddish orange in color.

Plants of the new *Begonia* can be compared to plants of the female parent selection. Plants of the new *Begonia* differ primarily from plants of the female parent selection in the following characteristics:

1. Plants of the new *Begonia* are more compact than plants of the female parent selection.
2. Leaves of plants of the new *Begonia* are smooth whereas leaves of plants of the female parent selection are uneven and have small bumps.

Plants of the new *Begonia* can be compared to plants of the male parent selection. Plants of the new *Begonia* differ primarily from plants of the male parent selection in the following characteristics:

1. Plants of the new *Begonia* are more rounded than plants of the male parent selection.
2. Plants of the new *Begonia* are more freely branching than plants of the male parent selection.

3. Plants of the new *Begonia* have double-type male flowers whereas plants of the male parent selection have single-type male flowers.

Plants of the new *Begonia* can be compared to plants of the *Begonia boliviensis* 'Veramente', not patented. In side-by-side comparisons, plants of the new *Begonia* differ from plants of 'Veramente' in the following characteristics:

1. Plants of the new *Begonia* are more compact than plants of 'Veramente'.
2. Plants of the new *Begonia* have darker green-colored leaves than plants of 'Veramente'.
3. Plants of the new *Begonia* have reddish orange-colored flowers whereas plants of 'Veramente' have bright red-colored flowers.

Plants of the new *Begonia* can also be compared to plants of the *Begonia boliviensis* 'Cinta', not patented. In side-by-side comparisons, plants of the new *Begonia* differ from plants of 'Cinta' in the following characteristics:

1. Plants of the new *Begonia* are more rounded than plants of 'Cinta'.
2. Plants of the new *Begonia* have darker green-colored leaves than plants of 'Cinta'.
3. Plants of the new *Begonia* have double-type male flowers whereas plants of 'Cinta' have single-type male flowers.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant. The photograph is a side perspective view of a typical flowering plant of 'BeTesnogat' grown in a container.

DETAILED BOTANICAL DESCRIPTION

Plants used for the aforementioned photograph and following observations and measurements were grown in 13-cm containers during the winter and early spring in a glass-covered greenhouse in Venhuizen, The Netherlands. Plants were 16 weeks old when the photograph and the description were taken. In the following description, color references are made to The Royal Horticultural Society Colour Chart, 2015 Edition, except where general terms of ordinary dictionary significance are used.

Botanical classification: *Begonia boliviensis* X *Begonia tuberhybrida* 'BeTesnogat'.

Parentage:

*Female, or seed, parent*.—Proprietary selection of *Begonia boliviensis* X *Begonia tuberhybrida* identified as code number 12-095-10, not patented.

*Male, or pollen, parent*.—Proprietary selection of *Begonia boliviensis* X *Begonia tuberhybrida* identified as code number 12-086-01, not patented.

Propagation:

*Type*.—By vegetative tip cuttings.

*Time to initiate roots, summer*.—About one week.

*Time to produce a rooted young plant, summer*.—About three to four weeks.

*Root description*.—Fine, fibrous; typically whitish in color, actual color of the roots is dependent on substrate composition, water quality, fertilizer type and formulation, substrate temperature and physiological age of roots; plants of the new *Begonia* have not been observed to form tubers.

*Rooting habit*.—Freely branching; dense.

Plant description:

*Plant and growth habit*.—Uniform, upright to broadly outwardly spreading plant habit; plant shape roughly flattened globular to spreading; freely branching habit with about five basal branches each with about five lateral branches developing per plant; moderately vigorous to vigorous growth habit and moderate growth rate.

*Plant height, soil level to top of foliar plane*.—About 23.2 cm.

*Plant height, soil level to top of floral plane*.—About 20.9 cm.

*Plant width*.—About 51.1 cm.

*Lateral branch description*.—Length: About 18.8 cm. Diameter: About 6 mm. Internode length: About 2.8 cm. Strength: Moderately weak, bending with the weight of the leaves and flowers. Aspect: Ranging from about 30° to about 85° from vertical. Texture and luster: Smooth, glabrous; moderately glossy. Color, developing: Close to 200D. Color, fully developed: Slightly darker than 148A; at the internodes, slightly darker than 148A tinged with close to 183A.

*Leaf description*.—Arrangement: Alternate, distichous; simple. Length: About 11.6 cm. Width: About 4.5 cm. Shape: Lanceolate. Apex: Narrowly acute. Base: Broadly oblique; lobes not imbricate. Margin: Dentate to serrate and doubly dentate to serrate. Texture and luster, upper surface: Smooth, glabrous; slightly velvety; slightly glossy. Texture and luster, lower surface: Smooth and mostly glabrous with sparse pubescence along midvein; slightly velvety; moderately glossy. Venation pattern: Pinnate. Color: Developing leaves, upper surface: Close to N199A tinged with darker than 148A. Developing leaves, lower surface: Close to 183B. Fully expanded leaves, upper surface: Slightly darker than N189A; venation, close to 138A. Fully expanded leaves, lower surface: Close to 183B; venation, close to N199A. Petioles: Length: About 2.4 cm. Diameter: About 3 mm. Texture and luster, upper and lower surfaces: Sparsely pubescent; moderately glossy. Strength: Low. Color, upper surface: Close to 177A; at leaf and stein attachment, close to 183C. Color, lower surface: Close to 177B. Stipules: Quantity per leaf: Two at the base of each leaf. Length: About 5 mm. Width: About 3 mm. Shape: Ovate to short oblong. Apex: Bluntly acute. Base: Broadly cuneate. Margins: Entire, ciliate. Color, upper and lower surfaces: Close to 147D; venation, close to 178B.

Flower description:

*Flowering habit*.—Rotate female flowers are single-types; rotate male flowers are double-types; flowers arranged in simple axillary cymes; freely flowering habit with about three flowers per cyme and about 500 flowers developing per plant during the flowering season; flowers face outwardly to nodding or drooping.

*Fragrance*.—None detected.

*Natural flowering season*.—Long flowering period; plants flower freely and continuously from spring into the autumn in The Netherlands; plants begin flowering about six weeks after pinching.

*Flower longevity*.—Individual flowers last about ten days on the plant; flowers not persistent.

*Inflorescence height* (*including peduncle*).—About 12.2 cm.

*Inflorescence diameter*.—About 10.4 cm.

*Flower buds, female flowers*.—Length: About 1.5 cm. Diameter, flattened: About 4 mm to 8 mm. Shape: Ovate; flattened. Texture and luster: Smooth, glabrous; velvety; matte. Color: Close to 37A; towards the base, close to 149C.

*Flower buds, male flowers*.—Length: About 1.9 cm. Diameter, flattened: About 9 mm to 14 mm. Shape: Roughly obovate; flattened. Texture and luster: Smooth, glabrous; velvety; matte. Color: Close to 42B.

*Female flowers*.—Size: About 5.4 cm by 5.4 cm. Depth: About 2.8 cm. Tepals: Quantity per flower and arrangement: Five in two whorls; inner whorl with three tepals and outer whorl with two tepals. Length, inner tepals: About 3.2 cm. Length, outer tepals: About 3.4 cm. Width, inner tepals: About 1.6 cm. Width, outer tepals: About 1.8 cm. Shape, inner tepals: Narrowly obovate to oblanceolate. Shape, outer tepals: Narrowly ovate to narrowly elliptic. Apex, inner tepals: Shallowly praemorse to rounded. Apex, outer tepals: Acute. Base, inner and outer tepals: Cuneate. Margin, inner and outer tepals: Entire; not undulate. Texture and luster, inner and outer tepals, upper surface: Smooth, glabrous; moderately velvety; matte. Texture and luster, inner and outer tepals, lower surface: Smooth, glabrous; moderately velvety; mostly matte with the base, slightly glossy. Color, inner and outer tepals: When opening, upper surface: Close to a blend of 42A and 43A. When opening, lower surface: Close to 42A. Fully opened, upper surface: Close to 43A; venation, close to 43A; color does not change with subsequent development. Fully opened, lower surface: Close to 43A; venation, close to 44A; color does not change with subsequent development. Tepaloids: None observed on female flowers.

*Male flowers*.—Size: About 6 cm by 6 cm. Depth: About 2.6 cm. Tepals: Quantity per flower and arrangement: Four in two whorls; inner whorl with two tepals and outer whorl with two tepals. Length, inner tepals: About 3.4 cm. Length, outer tepals: About 3.2 cm. Width, inner tepals: About 1.5 cm. Width, outer tepals: About 2 cm. Shape, inner tepals: Oblanceolate. Shape, outer tepals: Ovate to elliptic. Apex, inner tepals: Shallowly praemorse to rounded. Apex, outer tepals: Rounded. Base, inner and outer tepals: Cuneate. Margin, inner and outer tepals: Entire; not undulate. Texture and luster, inner and outer tepals, upper surface: Smooth, glabrous; moderately velvety; matte. Texture and luster, inner and outer tepals, lower surface: Smooth, glabrous; moderately velvety; mostly matte with the base, moderately glossy. Color, inner and outer tepals: When opening, upper surface: Close to 42A. When opening, lower surface: Close to 43A. Fully opened, upper surface: Close to 42A; venation, close to 42A; color does not change with subsequent development. Fully opened, lower surface: Close to 43B; venation, close to 44A; color becoming closer to 43C with subsequent development. Tepaloids: Quantity per flower and arrangement: About 26 at the center of the flower in about five whorls. Length: About 1.1 cm to 3 cm. Width: About 3 mm to 12 mm. Shape: Oblanceolate; slightly to moderately carinate. Apex: Obtuse to emarginate. Base: Narrowly cuneate. Margin: Entire; not undulate. Texture and luster, upper and lower surfaces: Smooth, glabrous; moderately velvety; matte. Color: When opening, upper and lower surfaces: Close to 42A; center, close to 3C. Fully opened, upper and lower surfaces: Close to 42A; venation, close to 42A; color does not change with subsequent development.

*Peduncles*.—Length: About 5.3 cm. Diameter: About 2 mm. Angle: About 60° from lateral branch axis. Strength: Moderately weak; flexible and bending with the weight of the flowers. Texture and luster: Smooth, glabrous; moderately glossy. Color, upper surface: Close to 178B. Color, lower surface: Close to 177B.

*Pedicels, female flowers*.—Length: About 3.4 cm. Diameter: About 1.5 mm. Angle: About 30° from the peduncle axis. Strength: Moderately weak; flexible, bending with the weight of the flowers. Texture and luster: Smooth, glabrous; glossy. Color, upper surface: Close to 34A. Color, lower surface: Close to 174B.

*Pedicels, male flowers*.—Length: About 2.5 cm. Diameter: About 1.5 mm. Angle: Mostly upright. Strength: Moderately weak; flexible, bending with the weight of the flowers. Texture and luster: Smooth, glabrous; glossy. Color, upper surface: Close to 34A. Color, lower surface: Close to 174B.

*Flower bracts*.—Quantity per flower and arrangement: Two, at the top of the peduncles. Length: About 7 mm. Width: About 7 mm. Shape: Broadly obovate. Apex: Rounded. Base: Broadly cuneate. Margin: Entire; ciliate. Texture and luster, upper and lower surfaces: Smooth, glabrous; slightly glossy. Color, upper and lower surfaces: Close to 179B.

*Reproductive organs*.—Androecium: Present only on male flowers. Stamen quantity per flower: If present, up to three. Filament length: About 3 mm. Filament color: Close to 11A. Anther size: About 1 mm by 1 mm. Anther shape: Obovate. Anther color: Close to 13A. Amount of pollen: None observed to date. Gynoecium: Present only on female flowers. Quantity per flower: Three; occasionally up to nine; pistils may be deformed. Pistil length: About 8 mm. Stigma diameter: About 4 mm. Stigma shape: Cleft or if deformed, not cleft. Stigma color: Close to 14A. Style length: About 5 mm to 7 mm. Style color: Close to 28A. Ovary color: Close to 144A tinged with close to N170B and at the apex, close to 173A. Seeds and fruits: To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BeTesnogat' as illustrated and described.

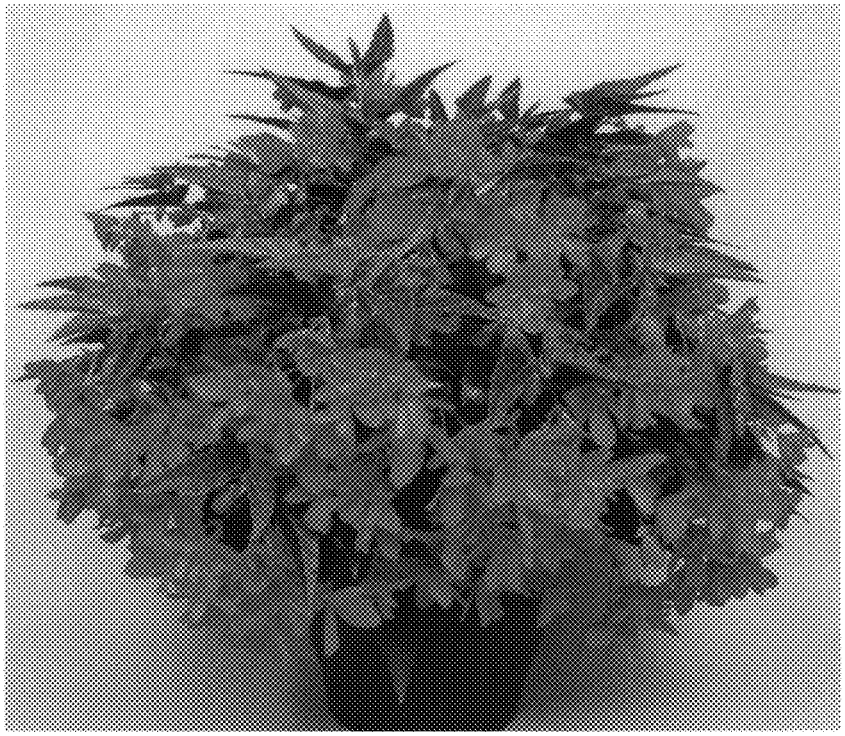

* * * * *